United States Patent [19]

Fischer, deceased et al.

[11] 4,113,939

[45] Sep. 12, 1978

[54] N',N'-DISUBSTITUTED 2,1,3-BENZOTHIADIAZIN-(4)-ONE-2,2-DIOXIDES

[75] Inventors: Adolf Fischer, deceased, late of Mutterstadt, Fed. Rep. of Germany, by Caecilia Emma Fischer, heiress-at-law; Gerhard Hamprecht, Mannheim, Fed. Rep. of Germany

[73] Assignee: BASF Aktiengesellschaft, Ludwigshafen, Fed. Rep. of Germany

[21] Appl. No.: 636,162

[22] Filed: Nov. 28, 1975

[30] Foreign Application Priority Data

Dec. 10, 1974 [DE] Fed. Rep. of Germany ....... 2458343

[51] Int. Cl.² .......................................... C07D 285/16
[52] U.S. Cl. .......................................... 544/11; 71/86; 71/87; 71/91
[58] Field of Search ...................... 260/243 R; 544/11

[56] References Cited

U.S. PATENT DOCUMENTS

| | | | |
|---|---|---|---|
| 3,041,336 | 6/1962 | Tewfel | 260/243 R |
| 3,217,001 | 11/1965 | Santilli et al. | 260/243 R |
| 3,708,277 | 1/1973 | Zeidler et al. | 260/243 R X |
| 3,822,257 | 7/1974 | Hamprecht et al. | 260/243 R |
| 3,935,200 | 1/1976 | Fischer et al. | 260/243 R |
| 3,940,389 | 2/1976 | McKendry et al. | 260/243 R |
| 3,997,531 | 12/1976 | Fischer et al. | 260/243 R |
| 4,075,004 | 2/1978 | Hamprecht et al. | 544/11 X |

*Primary Examiner*—Ethel G. Love
*Attorney, Agent, or Firm*—Keil, Thompson & Shurtleff

[57] ABSTRACT

Valuable substituted 2,1,3-benzothiadiazin-(4)-one-2,2-dioxides having a herbicidal action, herbicides containing these active ingredients, a process for controlling the growth of unwanted plants with these compounds, and processes for their manufacture.

9 Claims, No Drawings

N',N'-DISUBSTITUTED 2,1,3-BENZOTHIADIAZIN-(4)-ONE-2,2-DIOXIDES

The present invention relates to new and valuable substituted 2,1,3-benzothiadiazin-(4)-one-2,2-dioxides having a herbicidal action, herbicides containing these active ingredients, a process for controlling the growth of unwanted plants with these compounds, and processes for their manufacture.

It is known (German Pat. No. 1,542,836) that 3-isopropyl-2,1,3-benzothiadiazin-(4)-one-2,2-dioxide has a herbicidal action. However, it causes damage to crop plants.

We have now found that compounds of the formula

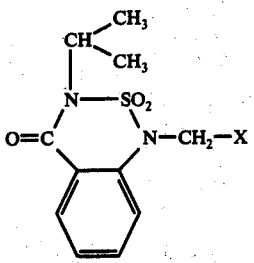
IV, where X denotes halogen or a

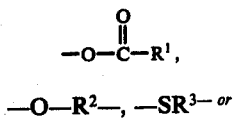

—O—R², —SR³— or

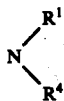

group, R¹ denoting alkyl, alkenyl, alkynyl, alkoxyalkyl, haloalkyl, cycloalkyl, aralkyl or optionally substituted aryl, R² denoting aralkyl, optionally substituted aryl, O,O-dialkylphosphoro, O,S-dialkylphosphoro, S,S-dialkylphosphoro, O,O-dialkylthiophosphoro, O,S-dialkylthiophosphoro and S,S-dialkylthiophosphoro, R³ having the same meanings as R¹ and additionally denoting O,O-dialkylthiophosphoro, O,S-dialkylthiophosphoro, S,S-dialkylthiophosphoro, O,O-dialkylphosphoro, O,S-dialkylphosphoro and S,S-dialkylphosphoro, and R⁴ denoting hydrogen or alkyl, it being possible for R⁴ and R¹ together to denote a heterocyclic ring, are better tolerated by the crop plants and afford the same weed control as the prior art compound.

The new N,N'-disubstituted 2,1,3-benzothiadiazin-(4)-one-2,2-dioxides of the formula IV are obtained by reacting a 2,1,3-benzothiadiazin-(4)-one-2,2-dioxide of the formula

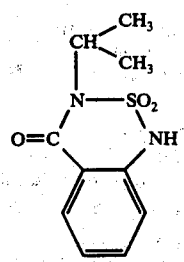
I with formaldehyde, or substances releasing formaldehyde, in the presence of an acid catalyst in inert solvents, and subsequently with a halogenating agent to give a compound of the formula

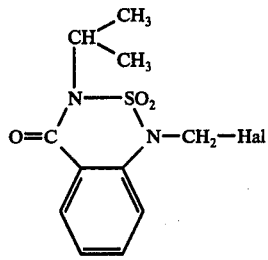
IVa,

Hal denoting halogen (method a), or by reacting the compounds of the formula IVa thus obtained with phenols, thiophenols, mercaptans, carboxylic acids, amines or phosphoric acid esters of the formula

H—X    II, where X has the above meanings except for "halogen", in the presence of an acid binder and optionally in the presence of a solvent (method b), or by reacting a 1-halomethyl-3-isopropyl-2,1,3-benzothiadiazin-(4)-one-2,2-dioxide of the formula IVa with a compound of the formula

A—X    III, where X has the above meanings except for "halogen" and A denotes an ammonium or alkylammonium ion or a cation selected from the group consisting of the alkali metals and alkaline earth metals, in the presence of a solvent (method c).

Examples of meanings for X are fluoro, chloro, bromo, iodo, formyloxy, acetoxy, chloroacetoxy, dichloroacetoxy, trichloroacetoxy, propionyloxy, 3-chloropropionyloxy, 2-chloropropionyloxy, 2,2-dichloropropionyloxy, butyryloxy, isobutyryloxy, 2-methylbutyryloxy, pivalyloxy, 2-chloro-3,3-dimethylbutyryloxy, valeryloxy, isovaleryloxy, sec-valeryloxy, capronyloxy, α-methylvaleryloxy, enanthyloxy, octanoyloxy, nonanoyloxy, decanoyloxy, dodecanoyloxy, tetradecanoyloxy, pentadecanoyloxy, octadecanoyloxy, 3-acetopropionyloxy, 3-methoxycarbonylpropionyloxy, 2-ethylcapronyloxy, acryloyloxy, buten-(2)-oyloxy, methoxyacetoxy, β-methoxypropionyloxy, propionlyloxy, cyclohexanoyloxy, benzoyloxy, α-naphthoyloxy, o,m,p-bromobenzoyloxy, o,m,p-nitrobenzoyloxy, 3,5-dichlorobenzoyloxy, p-tert-butylbenzoyloxy, p-methoxybenzoyloxy, phenylacetoxy, 4-chlorophenoxyacetoxy, 2,4-dichlorophenoxyacetoxy, 2,4,5-trichlorophenoxyacetoxy, 2-methyl-4-chlorophenoxyacetoxy, oxalyl, succinyl, phenoxy, o,m,p-cresyl, o,m,p-nitrophenoxy, o,m,p-chlorophenoxy, benzyloxy, 2,4-dichlorophenoxy, 3,5-dichlorophenoxy, 2,4,6-trichlorophenoxy, 3-methoxycarbonylaminophenoxy, (3,3-dimethylureido)-m-phenoxy, o,m,p-methoxyphenoxy, 4-chloro-2-methylphenoxy, phenylthio, o,m,p-chlorophenylthio, 2,4-dichlorophenylthio, 2,4,6-trichlorophenylthio, o,m,p-thiocresyl, o,m,p-nitrophenylthio, p-methoxyphenylthio, 4-chloro-2-methylphenylthio, methylthio, ethylthio, propylthio, isopropylthio, butylthio, isobutylthio, sec-butylthio, tert-butylthio, 3-propenylthio, benzylthio, 3-chloropropylthio, 3-methoxypropylthio, O,O-dimethylphosphorodithio, O,O-diethylphosphorodithio, O,O-di-n-propylphosphorodithio, O,O-diisopropylphosphorodithio, O,S-dimethylphosphorodithio, O,S-diethylphosphorodithio, S,S-dimethylphosphorodithio, S,S-diethylphosphorodithio, O,O-dimethylphosphorothio-S, O,O-diethylphosphorothio-S, O,S-dimethylphosphorothio-S, S,S-dimethylphosphorothio-S, O,O-dimethylphosphoro, O,O-diethylphosphoro, O,S-dimethylphosphoro, S,S-dimethylphosphoro, S,S-diethylphosphoro, O,O-dimethylthiophosphoro-O, O,S-dimethylthiophosphoro-O, S,S-dimethylthiophosphoro-O, 2,4-dinitro-6-bromoanilino, o-cyanoanilino, o-nitroanilino, o-bromo-p-nitroanilino, N-methyl-(o-bromo-p-nitroanilino), 3-isopropyl-2,1,3-benzothiadiazin-(4)-one-2,2-dioxide-1-yl.

If the starting materials are 3-isopropyl-2,1,3-benzothiadiazin-(4)-one-2,2-dioxide, paraformaldehyde, hydrogen chloride and/or thionyl chloride, the reaction may be illustrated by the following scheme:

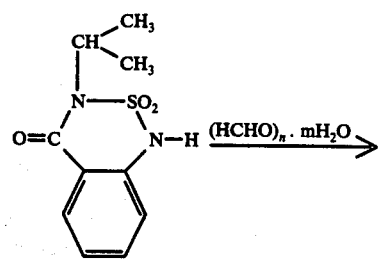

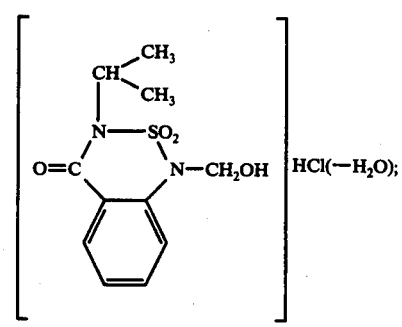

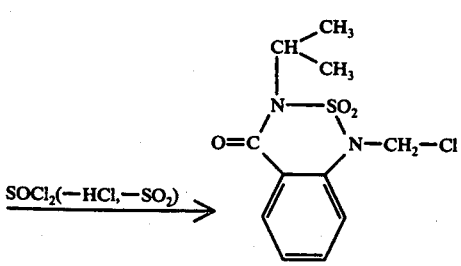

If the starting materials are 1-chloromethyl-3-isopropyl-2,1,3-benzothiadiazin-(4)-one-2,2-dioxide and potassium acetate, the reaction may be illustrated by the following scheme:

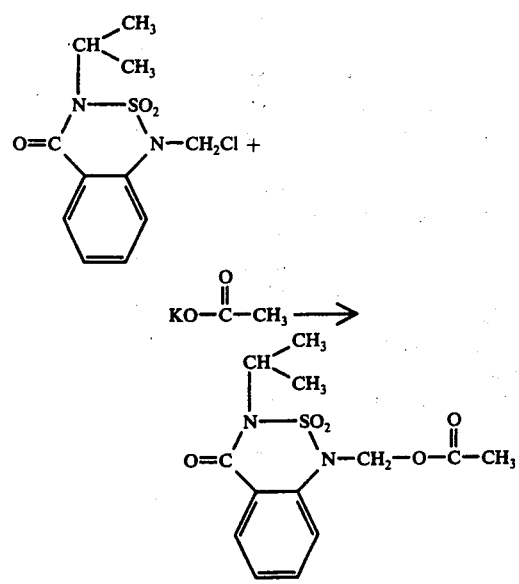

If the starting materials are 1-chloromethyl-3-isopropyl-2,1,3-benzothiadiazin-(4)-one-2,2-dioxide and isopropyl mercaptan, the reaction proceeds as follows:

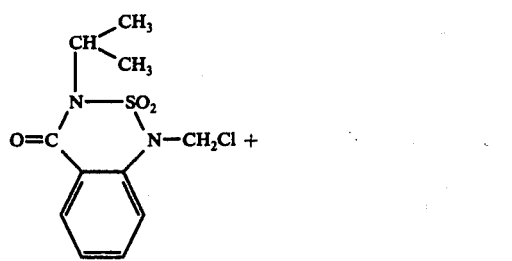

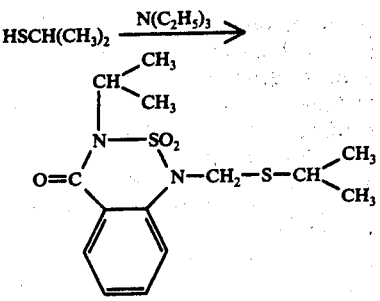

Examples of substances yielding formaldehyde are paraformaldehyde and/or trioxane.

Preferred halogenating agents are hydrogen halides such as hydrogen fluoride, hydrogen chloride, hydrogen bromide and hydrogen iodide, and/or inorganic acid chlorides, e.g., phosphorous trichloride, phosphorus pentachloride, phosphorus oxychloride, phosphorus tribromide, thionyl chloride, thionyl bromide, sulfur tetrafluoride, phosgene and carbonyl difluoride.

In a preferred embodiment of method a, a 3-isopropyl-2,1,3-benzothiadiazin-(4)-one-2,2-dioxide is mixed with at least 1 mole of formaldehyde or a compound yielding formaldehyde and a hydrogen halide or a Lewis acid, if desired in the presence of an inert solvent, at a temperature of from −10° to +120° C, preferably 0° to 50° C, and for from 1 to 10 hours; the product is then reacted with an excess of hydrogen halide to remove water or with an inorganic acid chloride at from −50° to +120° C, preferably 0° to 100° C, for from 1 to 12 hours.

Examples of inert solvents preferred in method *a* are hydrocarbons, such as ligroin, benzene, toluene; halohydrocarbons, such as methylene chloride, chloroform, 1,2-dichloroethane; ethers, such as diethyl ether, dioxane, tetrahydrofuran; and esters, such as acetoacetic ester, ethyl acetate and isobutyl acetate.

Suitable acid catalysts in addition to hydrogen halides such as hydrogen fluoride, hydrogen chloride, hydrogen bromide and hydrogen iodide are Lewis acids, such as iron (III) chloride, zinc(II) chloride and aluminum-(III) chloride, If phosgene or carbonyl fluoride is used, it is advantageous to add as the halogenation catalyst secondary carboxamides such as dimethyl formamide or dimethyl acetamide. The Lewis acids and carboxamides used as catalyst are advantageously employed in amounts of from 0.005 to 0.05 mole per mole of starting material I.

The phenols, thiophenols, mercaptans, carboxylic acids, phosphoric acid esters and amines and salts thereof of the formulae II and III used as starting materials for method *b* are known.

The acid binder may be any conventional acid binding agent; it is however preferred to use alkali metal hydroxides, alkali metal carbonates and tertiary organic bases. Particularly suitable compounds are sodium carbonate, triethylamine, pyridine, trimethylamine, α, β, γ-picoline, lutidine, N,N-dimethylaniline, N,N-dimethylcyclohexylamine, quinoline, tri-n-propylamine and tri-n-butylamine.

The reaction temperature in method *b* may be varied within a wide range. It is generally from −20° to +100° C, preferably from −10° to 80° C.

In method *b* of the process of the invention there is for instance reacted 1 mole of 1-halomethyl-3-isopropyl-2,1,3-benzothiadiazin-(4)-one-2,2-dioxide of the formula IV a with 1 mole of a compound of the formula II and from 1 to about 1.2 moles of an acid binder. Further variations in the stoichiometric ratio offer no essential improvement in yield.

Suitable solvents for method *b* are the same inert organic solvents used in method *a*.

In method *c* of the process of the invention, there is for instance reacted from 1 to 2 moles of a compound of the formula III with 1 mole of a compound of the formula IV a. The reaction temperature is in general from 0° to 120° C, preferably 20° to 100° C. Particularly suitable solvents for method *c* are polar organic solvents. Preferred examples are nitriles, such as acetonitrile, isobutyronitrile and benzonitrile; sulfoxides, such as dimethyl sulfoxide; amides, such as dimethylformamide and N-methylpyrrolidone; and esters, such as ethyl acetate and isobutyl acetate.

To isolate the compounds of the formula IV *a* the reaction mixture is freed in vacuo from excess halogenating agent, formaldehyde and solvent, and the residue is recrystallized. It is, however, often possible to react the crude products of the formula IV *a* remaining after removal of the solvent direct with the starting materials of the formulae II or III.

To isolate the compounds of the formula IV *a* from the reaction mixture in methods *b* and *c* of the process of the invention, the precipitated halide is separated and the filtrate concentrated to dryness. The residue is taken up in a water-immiscible solvent and extracted briefly with dilute aqueous alkaline solution and then with water. If the amount of polar water-immiscible diluent used is small, the reaction solution may also be extracted direct with dilute aqueous alkali solution and water. The desired end products are obtained after the organic phase has been dried and concentrated. If necessary, they may be further purified in conventional manner, e.g., by recrystallization or chromatography.

EXAMPLE 1

1-chloromethyl-3-isopropyl-2,1,3-benzothiadiazin-(4)-one-2,2-dioxide

At 5° to 10° C, a suspension of 7.0 parts (by weight) of paraformaldehyde and 24 parts of 3-isopropyl-2,1,3-benzothiadiazin-(4)-one-2,2-dioxide in 260 parts of benzene is saturated, while stirring, with hydrogen chloride. Subsequently, 28.0 parts of thionyl chloride is run in over a period of 20 minutes, whereupon the temperature rises to 15° C. The mixture is then stirred for 12 hours at room temperature until no more gas evolves, and is then concentrated in vacuo. The crystalline residue is recrystallized from cyclohexane. There is obtained 25 parts (87% of theory) of the desired compound; m.p.: 116° to 122° C.

EXAMPLE 2

1-chloromethyl-3-isopropyl-2,1,3-benzothiadiazin-(4)-one-2,2-dioxide

While stirring and at 5° to 10° C, a suspension of 24 parts of 3-isopropyl-2,1,3-benzothiadiazin-(4)-one-2,2-dioxide and 8.0 parts of paraformaldehyde in 260 parts of benzene is saturated with hydrogen chloride. 0.365 part of dimethylformamide is added and the reaction solution treated over a period of 1 hour with 24 parts of phosgene; the mixture is terminally heated to 45° C. Excess phosgene is expelled with nitrogen. The reaction solution is washed with 100 parts of water, 100 ml of 0.5N caustic soda solution and again with 100 parts of water, dried over magnesium sulfate and concentrated in vacuo. There is obtained 26 parts (90% of theory) of the desired compound, m.p.: 110° to 118° C.

EXAMPLE 3

1-bromomethyl-3-isopropyl-2,1,3-benzothiadiazin-(4)-one-2,2-dioxide

While stirring and at 5° to 10° C, a suspension of 9.0 parts of paraformaldehyde and 24 parts of 3-isopropyl-2,1,3-benzothiadiazin-(4)-one-2,2-dioxide in 280 parts of benzene is saturated with hydrogen chloride. Subsequently, 81.3 parts of phosphorus tribromide is added over a period of 15 minutes at 15° C. The mixture is stirred for 3 hours at room temperature and for 3 hours at 50° C. After excess solvent has been removed in vacuo, the residue is recrystallized from cyclohexane; the desired product is obtained in the form of colorless crystals melting at 108° to 111° C.

EXAMPLE 4

1-chloromethyl-3-isopropyl-2,1,3-benzothiadiazin-(4)-one-2,2-dioxide

At 5° to 10° C and while stirring, a suspension of 24.0 parts of 3-isopropyl-2,1,3-benzothiadiazin-(4)-one-2,2-dioxide and 9.0 parts of paraformaldehyde in 280 parts of benzene is saturated with hydrogen chloride. The clear solution which forms is subsequently treated for a further 30 minutes at 25° C with hydrogen chloride. After the solution has been stirred for 1 hour at 25° C it is concentrated in vacuo and the residue taken up in 250 parts of benzene. The organic phase is extracted three times with 0.5N caustic soda solution, each time in an amount of 100 ml, and with water. After drying over magnesium sulfate and concentration in vacuo there is obtained 21 parts (73% of theory) of the desired compound as colorless crystals; m.p.: 110° to 119° C.

The following compounds were obtained analogously:

1-fluoromethyl-3-isopropyl-2,1,3-benzothiadiazin-(4)-one-2,2-dioxide 1-iodomethyl-3-isopropyl-2,1,3-benzothiadiazin-(4)-one-2,2-dioxide.

EXAMPLE 5

1-(acetoxy)-methyl-3-isopropyl-2,1,3-benzothiadiazin-(4)-one-2,2-dioxide

At room temperature and while stirring, 9.8 parts of potassium acetate was introduced in portions into a solution of 28.8 parts of 1-chloromethyl-3-isopropyl-2,1,3-benzothiadiazin-(4)-one-2,2-dioxide in 160 parts of acetonitrile. The mixture was stirred for 5 hours at 80° C. The potassium chloride which has precipitated out was removed and the organic phase concentrated. Subsequently, the oily residue was taken up in benzene, washed twice with 10% aqueous sodium hydrogen carbonate solution and with water, and dried over magnesium sulfate. After concentration there was obtained 25 parts (82% of theory) of the desired compound as colorless crystals; m.p.: 100° to 104° C.

The following compounds were obtained analogously:

| | m.p. (° C) |
|---|---|
| 1-(formyloxy)-methyl-3-isopropyl-2,1,3-benzothiadiazin-(4)-one-2,2-dioxide | 99–104 |
| 1-(chloroacetoxy)-methyl-3-isopropyl-2,1,3-benzothiadiazin-(4)-one-2,2-dioxide | 78–85 |
| 1-(dichloroacetoxy)-methyl-3-isopropyl-2,1,3-benzothiadiazin-(4)-one-2,2-dioxide | |
| 1-(trichloroacetoxy)-methyl-3-isopropyl-2,1,3-benzothiadiazin-(4)-one-2,2-dioxide | |
| 1-(propionyloxy)-methyl-3-isopropyl-2,1,3-benzothiadiazin-(4)-one-2,2-dioxide | |
| 1-(3'-chloropropionyloxy)-methyl-3-isopropyl-2,1,3-benzothiadiazin-(4)-one-2,2-dioxide | |
| 1-(2'-chloropropionyloxy)-methyl-3-isopropyl-2,1,3-benzothiadiazin-(4)-one-2,2-dioxide | |
| 1-(2'-2'-dichloropropionyloxy)-methyl-3-isopropyl-2,1,3-benzothiadiazin-(4)-one-2,2-dioxide | |
| 1-(butyryloxy)-methyl-3-isopropyl-2,1,3-benzothiadiazin-(4)-one-2,2-dioxide | |
| 1-(isobutyryloxy)-methyl-3-isopropyl-2,1,3-benzothiadiazin-(4)-one-2,2-dioxide | $n_D^{27} = 1.5235$ |
| 1-(2'-methylbutyryloxy)-methyl-3-isopropyl-2,1,3-benzothiadiazin-(4)-one-2,2-dioxide | |
| 1-(pivalyloxy)-methyl-3-isopropyl-2,1,3-benzothiadiazin-(4)-one-2,2-dioxide | |
| 1-(2'-chloro-3',3-dimethylbutyryloxy)-methyl-3-isopropyl-2,1,3-benzothiadiazin-(4)-one-2,2-dioxide | |
| 1-(valeryloxy)-methyl-3-isopropyl-2,1,3-benzothiadiazin-(4)-one-2,2-dioxide | |
| 1-(isovaleryloxy)-methyl-3-isopropyl-2,1,3-benzothiadiazin-(4)-one-2,2-dioxide | |
| 1-(sec-valeryloxy)-methyl-3-isopropyl-2,1,3-benzothiadiazin-(4)-one-2,2-dioxide | |
| 1-(capronyloxy)-methyl-3-isopropyl-2,1,3-benzothiadiazin-(4)-one-2,2-dioxide | |
| 1-(α-methylvaleryloxy)-methyl-3-isopropyl-2,1,3-benzothiadiazin-(4)-one-2,2-dioxide | |
| 1-(enanthyloxy)-methyl-3-isopropyl-2,1,3-benzothiadiazin-(4)-one-2,2-dioxide | |
| 1-(octanoyloxy)-methyl-3-isopropyl-2,1,3-benzothiadiazin-(4)-one-2,2-dioxide | |
| 1-(nonanoyloxy)-methyl-3-isopropyl-2,1,3-benzothiadiazin-(4)-one-2,2-dioxide | |
| 1-(decanoyloxy)-methyl-3-isopropyl-2,1,3-benzothiadiazin-(4)-one-2,2-dioxide | |
| 1-(dodecanoyloxy)-methyl-3-isopropyl-2,1,3-benzothiadiazin-(4)-one-2,2-dioxide | |

-continued

| | m.p. (° C) |
|---|---|
| 1-(tetradecanoyloxy)-methyl-3-isopropyl-2,1,3-benzothiadiazin-(4)-one-2,2-dioxide | |
| 1-(pentadecanoyloxy)-methyl-3-isopropyl-2,1,3-benzothiadiazin-(4)-one-2,2-dioxide | |
| 1-(octadecanoyloxy)-methyl-3-isopropyl-2,1,3-benzothiadiazin-(4)-one-2,2-dioxide | |
| 1-(3'-acetopropionyloxy)-methyl-3-isopropyl-2,1,3-benzothiadiazin-(4)-one-2,2-dioxide | |
| 1-(3'-methoxycarbonylpropionyloxy)-methyl-3-isopropyl-2,1,3-benzothiadiazin-(4)-one-2,2-dioxide | |
| 1-(2'-ethylcapronyloxy)-methyl-3-isopropyl-2,1,3-benzothiadiazin-(4)-one-2,2-dioxide | |
| 1-(acryloyloxy)-methyl-3-isopropyl-2,1,3-benzothiadiazin-(4)-one-2,2-dioxide | 48–50 |
| 1-(buten-(2)-oyloxy)-methyl-3-isopropyl-2,1,3-benzothiadiazin-(4)-one-2,2-dioxide | |
| 1-(methoxyacetoxy)-methyl-3-isopropyl-2,1,3-benzothiadiazin-(4)-one-2,2-dioxide | $n_D^{25} = 1.5330$ |
| 1-(β-methoxypropionyloxy)-methyl-3-isopropyl-2,1,3-benzothiadiazin-(4)-one-2,2-dioxide | |
| 1-(propioloyloxy)-methyl-3-isopropyl-2,1,3-benzothiadiazin-(4)-one-2,2-dioxide | 110–118 |
| 1-(cyclohexanoyloxy)-methyl-3-isopropyl-2,1,3-benzothiadiazin-(4)-one-2,2-dioxide | 65–71 |
| 1-(benzoyloxy)-methyl-3-isopropyl-2,1-3 benzothiadiazin-(4)-one-2,2-dioxide | 109–111 |
| 1-(α-napthoyloxy)-methyl-3-isopropyl-2,1,3-benzothiadiazin-(4)-one-2,2-dioxide | |
| 1-(o-bromobenzoyloxy)-methyl-3-isopropyl-2,1,3-benzothiadiazin-(4)-one-2,2-dioxide | |
| 1-(m-bromobenzoyloxy)-methyl-3-isopropyl-2,1,3-benzothiadiazin-(4)-one-2,2-dioxide | |
| 1-(p-bromobenzoyloxy)-methyl-3-isopropyl-2,1,3-benzothiadiazin-(4)-one-2,2-dioxide | |
| 1-(3',5-dichlorobenzoyloxy)-methyl-3-isopropyl-2,1,3-benzothiadiazin-(4)-one-2,2-dioxide | 153–158 |
| 1-(o-nitrobenzoyloxy)-methyl-3-isopropyl-2,1,3-benzothiadiazin-(4)-one-2,2-dioxide | |
| 1-(m-nitrobenzoyloxy)-methyl-3-isopropyl-2,1,3-benzothiadiazin-(4)-one-2,2-dioxide | |
| 1-(p-nitrobenzoyloxy)-methyl-3-isopropyl-2,1,3-benzothiadiazin-(4)-one-2,2-dioxide | 145–148 |
| 1-(p-tert-butylbenzoyloxy)-methyl-3-isopropyl-2,1,3-benzothiadiazin-(4)-one-2,2-dioxide | |
| 1-(p-methoxybenzoyloxy)-methyl-3-isopropyl-2,1,3-benzothiadiazin-(4)-one-2,2-dioxide | 106–110 |
| 1-(phenylacetoxy)-methyl-3-isopropyl-2,1,3-benzothiadiazin-(4)-one-2,2-dioxide | |
| 1-(4'-chlorophenoxyacetoxy)-methyl-3-isopropyl-2,1,3-benzothiadiazin-(4)-one-2,2-dioxide | |
| 1-(2',4'-dichlorophenoxyacetoxy)-methyl-3-isopropyl-2,1,3-benzothiadiazin-(4)-one-2,2-dioxide | |
| 1-(2',4',5'-trichlorophenoxyacetoxy)-methyl-3-isopropyl-2,1,3-benzothiadiazin-(4)-one-2,2-dioxide | |
| 1-(2'-methyl-4'-chlorophenoxyacetoxy)-methyl-3-isopropyl-2,1,3-benzothiadiazin-(4)-one-2,2-dioxide | |
| oxalyl-bis-1-(methyl-3-isopropyl-2,1,3-benzothiadiazin-(4)-one-2,2-dioxide) | |
| succinyl-bis-1-(methyl-3-isopropyl-2,1,3-benzothiadiazin-(4)-one-2,2-dioxide) | |

EXAMPLE 6

1-(p-nitrophenoxy)-methyl-3-isopropyl-2,1,3-benzothiadiazin-(4)-one-2,2-dioxide

At room temperature and while stirring, 12.8 parts of the sodium salt of p-nitrophenol is introduced in portions into a solution of 23.1 parts of 1-chloromethyl-3-isopropyl-2,1,3-benzothiadiazin-(4)-one-2,2-dioxide in 160 parts of acetonitrile. The mixture is stirred under reflux for 3 hours and then concentrated in vacuo. The residue is taken up in methylene chloride and washed three times with 0.3N caustic soda solution, each time with 100 ml, and with water. After drying over magnesium sulfate, concentration in vacuo and trituration with cyclohexane there is obtained 30 parts (96% of theory) of the desired compound; m.p.: 133° to 140° C.

The following compounds were obtained analogously:

| | m.p. (° C) |
|---|---|
| 1-(o-chlorophenoxy)-methyl-3-isopropyl-2,1,3-benzothiadiazin-(4)-one-2,2-dioxide | |
| 1-(p-chlorophenoxy)-methyl-3-isopropyl-2,1,3-benzothiadiazin-(4)-one-2,2-dioxide | |
| 1-(m-chlorophenoxy)-methyl-3-isopropyl-2,1,3-benzothiadiazin-(4)-one-2,2-dioxide | |
| 1-(2',4'-dichlorophenoxy)-methyl-3-isopropyl-2,1,3-benzothiadiazin-(4)-one-2,2-dioxide | 108–112 |
| 1-(3',5'-dichlorophenoxy)-methyl-3-isopropyl-2,1,3-benzothiadiazin-(4)-one-2,2-dioxide | |
| 1-(2',4',6'-trichlorophenoxy)-methyl-3-isopropyl-2,1,3-benzothiadiazin-(4)-one-2,2-dioxide | 198–203 |
| 1-(phenoxy)-methyl-3-isopropyl-2,1,3-benzothiadiazin-(4)-one-2,2-dioxide | 71–78 |
| 1-(o-cresyl)-methyl-3-isopropyl-2,1,3-benzothiadiazin-(4)-one-2,2-dioxide | |
| 1-(m-cresyl)-methyl-3-isopropyl-2,1,3-benzothiadiazin-(4)-one-2,2-dioxide | |
| 1-(p-cresyl)-methyl-3-isopropyl-2,1,3-benzothiadiazin-(4)-one-2,2-dioxide | |
| 1-(o-nitrophenoxy)-methyl-3-isopropyl-2,1,3-benzothiadiazin-(4)-one-2,2-dioxide | |
| 1-(3'-methoxycarbonylaminophenoxy)-methyl-3-isopropyl-2,1,3-benzothiadiazin-(4)-one-2,2-dioxane | 56–64 |
| 1-((3',3'-dimethylureido)-m-phenoxy)-methyl-3-isopropyl-2,1,3-benzothiadiazin-(4)-one-2,2-dioxide | 128–133 |
| 1-(m-nitrophenoxy)-methyl-3-isopropyl-2,1,3-benzothiadiazin-(4)-one-2,2-dioxide | |
| 1-(o-methoxyphenoxy)-methyl-3-isopropyl-2,1,3-benzothiadiazin-(4)-one-2,2-dioxide | |
| 1-(p-methoxyphenoxy)-methyl-3-isopropyl-2,1,3-benzothiadiazin-(4)-one-2,2-dioxide | |
| 1-(m-methoxyphenoxy)-methyl-3-isopropyl-2,1,3-benzothiadiazin-(4)-one-2,2-dioxide | |
| 1-(4'-chloro-2'-methylphenoxy)-methyl-3-isopropyl-2,1,3-benzothiadiazin-(4)-one-2,2-dioxide | |
| 1-(benzyloxy)-methyl-3-isopropyl-2,1,3-benzothiadiazin-(4)-one-2,2-dioxide | $n_D^{25} = 1.5649$ |

EXAMPLE 7

1-(p-chlorophenylthio)-methyl-3-isopropyl-2,1,3-benzothiadiazin-(4)-one-2,2-dioxide At 20° to 25° C and while stirring, 15.5 parts of triethylamine was introduced through a feed means at the same rate as 21.7 parts of p-chlorothiophenol dissolved in 20 parts of acetonitrile through another feed means into a solution of 43.2 parts of 1-chloromethyl-3-isopropyl-2,1,3-benzothiadiazin-(4)-one-2,2-dioxide in 240 parts of acetonitrile. This mixture was stirred for 12 hours at room temperature and then freed from solvent in vacuo. The residue was taken up in 250 parts of benzene and washed twice with 1N caustic soda solution, each time with 50 ml, and with water. After drying, concentration, and trituration with petroleum ether, there was isolated 52 parts (87% of theory) of the desired product; m.p.: 59° to 64° C.

The following compounds were obtained analogously:

| | m.p. (° C) |
|---|---|
| 1-(o-chlorophenylthio)-methyl-3-isopropyl-2,1,3-benzothiadiazin-(4)-one-2,2-dioxide | |
| 1-(m-chlorophenylthio)-methyl-3-isopropyl-2,1,3-benzothiadiazin-(4)-one-2,2-dioxide | |
| 1-(phenylthio)-methyl-3-isopropyl-2,1,3-benzothiadiazin-(4)-one-2,2-dioxide | $n_D^{25} = 1.5935$ |
| 1-(2',4'-dichlorophenylthio)-methyl-3-isopropyl-2,1,3-benzothiadiazin-(4)-one-2,2-dioxide | |
| 1-(2',4',6'-trichlorophenylthio)-methyl-3-isopropyl-2,1,3-benzothiadiazin-(4)-one-2,2-dioxide | |
| 1-(o-thiocresyl)-methyl-3-isopropyl-2,1,3-benzothiadiazin-(4)-one-2,2-dioxide | |
| 1-(p-thiocresyl)-methyl-3-isopropyl-2,1,3-benzothiadiazin-(4)-one-2,2-dioxide | |
| 1-(m-thiocresyl)-methyl-3-isopropyl-2,1,3-benzothiadiazin-(4)-one-2,2-dioxide | |
| 1-(o-nitrophenylthio)-methyl-3-isopropyl-2,1,3-benzothiadiazin-(4)-one-2,2-dioxide | |
| 1-(m-nitrophenylthio)-methyl-3-isopropyl-2,1,3-benzothiadiazin-(4)-one-2,2-dioxide | |
| 1-(p-nitrophenylthio)-methyl-3-isopropyl-2,1,3-benzothiadiazin-(4)-one-2,2-dioxide | |
| 1-(p-methoxyphenylthio)-methyl-3-isopropyl-2,1,3-benzothiadiazin-(4)-one-2,2-dioxide | |
| 1-(4'-chloro-2'-methylphenylthio)-methyl-3-isopropyl-2,1,3-benzothiadiazin-(4)-one-2,2-dioxide | |
| 1-(methylthio)-methyl-3-isopropyl-2,1,3-benzothiadiazin-(4)-one-2,2-dioxide | |
| 1-(ethylthio)-methyl-3-isopropyl-2,1,3-benzothiadiazin-(4)-one-2,2-dioxide | |
| 1-(propylthio)-methyl-3-isopropyl-2,1,3-benzothiadiazin-(4)-one-2,2-dioxide | |
| 1-(isopropylthio)-methyl-3-isopropyl-2,1,3-benzothiadiazin-(4)-one-2,2-dioxide | 52–58 |
| 1-(butylthio)-methyl-3-isopropyl-2,1,3-benzothiadiazin-(4)-one-2,2-dioxide | |
| 1-(isobutylthio)-methyl-3-isopropyl-2,1,3-benzothiadiazin-(4)-one-2,2-dioxide | $n_D^{25} = 1.5411$ |
| 1-(sec-butylthio)-methyl-3-isopropyl-2,1,3-benzothiadiazin-(4)-one-2,2-dioxide | |
| 1-(tert-butylthio)-methyl-3-isopropyl-2,1,3-benzothiadiazin-(5)-one-2,2-dioxide | |
| 1-(3'-propenylthio)-methyl-3-isopropyl-2,1,3-benzothiadiazin-(4)-one-2,2-dioxide | |
| 1-(benzylthio)-methyl-3-isopropyl-2,1,3-benzothiadiazin-(4)-one-2,2-dioxide | |
| 1-(3'-chloropropylthio)-methyl-3-isopropyl-2,1,3-benzothiadiazin-(4)-one-2,2-dioxide | |
| 1-(3'-methoxypropylthio)-methyl-3-isopropyl-2,1,3-benzothiadiazin-(4)-one-2,2-dioxide | |

EXAMPLE 8

1-(O,O-dimethylphosphorodithio)-methyl-3-isopropyl-2,1,3-benzothiadiazin-(4)-one-2,2-dioxide At 10° C and while stirring, 28.9 parts of 1-chloromethyl-3-isopropyl-2,1,3-benzothiadiazin-(4)-one-2,2-dioxide dissolved in 120 parts of acetonitrile was introduced over a period of 30 minutes into a suspension of 18.0 parts of the sodium salt of O,O-dimethyldithiophosphoric acid ester in 200 parts of acetonitrile. The mixture was stirred for 12 hours at room temperature and for 3 hours at 55° C. After the solvent had been removed in vacuo, the residue was taken up in benzene and washed three times with 5% aqueous sodium carbonate solution and with water. After drying over magnesium sulfate and concentration in vacuo, the residue was triturated in a 4:1 mixture of benzene/petroleum ether; there was isolated 33 parts of the desired compound melting at from 79° to 84° C.

The following compounds were obtained analogously:

| | m.p. (° C) |
|---|---|
| 1-(O,O-diethylphosphorodithio)-methyl-3-isopropyl-2,1,3-benzothiadiazin-(4)-one-2,2-dioxide | 63–64 |
| 1-(O,O-di-n-propylphosphorodithio)-methyl-3-isopropyl-2,1,3-benzothiadiazin-(4)-one-2,2-dioxide | |
| 1-(O,O-di-isopropylphosphorodithio)-methyl-3-isopropyl-2,1,3-benzothiadiazin-(4)-one-2,2-dioxide | |
| 1-(O,S-dimethylphosphorodithio)-methyl-3-isopropyl-2,1,3-benzothiadiazin-(4)-one-2,2-dioxide | |
| 1-(O,S-diethylphosphorodithio)-methyl-3-isopropyl-2,1,3-benzothiadiazin-(4)-one-2,2-dioxide | |

| -continued | m.p. (° C) |
|---|---|
| 1-(S,S-dimethylphosphorodithio)-methyl-3-isopropyl-2,1,3-benzothiadiazin-(4)-one-2,2-dioxide | |
| 1-(S,S-diethylphosphorodithio)-methyl-3-isopropyl-2,1,3-benzothiadiazin-(4)-one-2,2-dioxide | |
| 1-(O,O-dimethylphosphorothio)-S-methyl-3-isopropyl-2,1,3-benzothiadiazin-(4)-one-2,2-dioxide | $n_D^{25} = 1.5455$ |
| 1-(O,O-diethylphosphorothio)-S-methyl-3-isopropyl-2,1,3-benzothiadiazin-(4)-one-2,2-dioxide | |
| 1-(O,S-dimethylphosphorothio)-S-methyl-3-isopropyl-2,1,3-benzothiadiazin-(4)-one-2,2-dioxide | |
| 1-(S,S-dimethylphosphorothio)-S-methyl-3-isopropyl-2,1,3-benzothiadiazin-(4)-one-2,2-dioxide | |
| 1-(O,O-dimethylphosphoro)-methyl-3-isopropyl-2,1,3-benzothiadiazin-(4)-one-2,2-dioxide | |
| 1-(O,O-diethylphosphoro)-methyl-3-isopropyl-2,1,3-benzothiadiazin-(4)-one-2,2-dioxide | |
| 1-(O,O-dimethylphosphoro)-methyl-3-isopropyl-2,1,3-benzothiadiazin-(4)-one-2,2-dioxide | |
| 1-(S,S-dimethylphosphoro)-methyl-3-isopropyl-2,1,3-benzothiadiazin-(4)-one-2,2-dioxide | |
| 1-(S,S-diethylphosphoro)-methyl-3-isopropyl-2,1,3-benzothiadiazin-(4)-one-2,2-dioxide | |
| 1-(O,O-dimethylthiophosphoro-O-methyl-3-isopropyl-2,1,3-benzothiadiazin-(4)-one-2,2-dioxide | |
| 1-(O,S-dimethylthiophosphoro)-O-methyl-3-isopropyl-2,1,3-benzothiadiazin-(4)-one-2,2-dioxide | |
| 1-(S,S-dimethylthiophosphoro)-O-methyl-3-isopropyl-2,1,3-benzothiadiazin-(4)-one-2,2-dioxide | |

EXAMPLE 9

1-(2',4'-dinitro-6'-bromoanilino)-methyl-3-isopropyl-2,1,3-benzothiadiazin-(4)-one-2,2-dioxide At 0° to 10° C and while stirring, 15.0 parts of triethylamine and a mixture of 39.3 parts of 2,4-dinitro-6-bromoaniline in 195 parts of acetonitrile were added simultaneously through 2 separate feed means to a solution of 43.2 parts of 1-chloromethyl-3-isopropyl-2,1,3-benzothiadiazin-(4)-one-2,2-dioxide in 235 parts of acetonitrile. The mixture was stirred for 1 ½ hours at room temperature and for 4 hours at 65° C and then concentrated in vacuo. The residue was taken up in ethyl acetate and washed twice with 100 ml of 1N caustic soda solution, four times with 100 ml of 0.3N hydrochloric acid, and with water. The desired compound was isolated after drying over magnesium sulfate; m.p.: 131° to 137° C.

The following compounds were obtained analogously:

1-(o-cyanoanilino)-methyl-3-isopropyl-2,1,3-benzothiadiazin-(4)-one-2,2-dioxide 1-(o-nitroanilino)-methyl-3-isopropyl-2,1,3-benzothiadiazin-(4)-one-2,2-dioxide 1-(o-bromo-p-nitroanilino)-methyl-3-isopropyl-2,1,3-benzothiadiazin-(4)-one-2,2-dioxide 1-(N-methyl-o-bromo-p-nitroanilino)-methyl-3-isopropyl-2,1,3-benzothiadiazin-(4)-one-2,2-dioxide

EXAMPLE 10

At room temperature, 4.32 parts of sodium methylate was introduced into a solution of 23.1 parts of 1-chloromethyl-3-isopropyl-2,1,3-benzothiadiazin-(4)-one-2,2-dioxide in 100 parts of acetonitrile. The mixture was stirred for 3 hours under reflux and then concentrated in vacuo. The residue was extracted with warm benzene and the filtrate precipitated with cyclohexane. There was obtained 1-bis-(3-isopropyl-2,1,3-benzothiadiazin-(4)-one-2,2-dioxide)-methane melting at 182° to 186° C.

Application of the new active ingredients may be effected for instance in the form of directly sprayable solutions, powders, suspensions (including high-percentage oily suspensions), dispersions, emulsions, oil dispersions, pastes, dusts, broadcasting agents, or granules by spraying, atomizing, dusting, broadcasting or watering. The forms of application depend entirely on the purpose for which the agents are being used; in any case they should ensure a fine distribution of the active ingredient.

For the preparation of solutions, emulsions, pastes and oil dispersions to be sprayed direct, mineral oil fractions of medium to high boiling point, such as kerosene or diesel oil, further coal-tar oils, etc. and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ether, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl, alcohol, fatty alcohol ethylene oxide condensates, athoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silica gel, silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90% by weight of active ingredient.

There may be added to the compositions or individual active ingredients (if desired, immediately before use (tankmix) ) oils of various types, herbicides, fungicides, nematocides, insecticides, bactericides, trace elements, fertilizers, antifoams (e.g., silicones), growth regulators, antidotes and other herbicidally effective compounds such as

- substituted anilines
- substituted aryloxycarboxylic acids and salts, esters and amides thereof
- substituted ethers
- substituted arsonic acids and their salts, esters and amides
- substituted benzimidazoles
- substituted benzisothiazoles
- substituted benzothiadiazinone dioxides
- substituted benzoxazines
- substituted benzoxazinones
- substituted benzothiadiazoles
- substituted biurets
- substituted quinolines
- substituted carbamates
- substituted aliphatic carboxylic acids and their salts, esters and amides
- substituted aromatic carboxylic acids and their salts, esters and amides
- substituted carbamoylalkylthiol- or -dithiophosphates
- substituted quinazolines
- substituted cycloalkylamidocarbothiolic acids and their salts esters and amides
- substituted cycloalkylcarbonamidothiazoles
- substituted dicarboxylic acids and their salts, esters and amides
- substituted dihydrobenzofuranyl sulfonates
- substituted disulfides
- substituted dipyridylium salts
- substituted dithiocarbamates
- substituted dithiophosphoric acids and their salts, esters and amides
- substituted ureas
- substituted hexahydro-1H-carbothioates
- substituted hydantoins
- substituted hydrazides
- substituted hydrazonium salts
- substituted isoxazole pyrimidones
- substituted imidazoles
- substituted isothiazole pyrimidones
- substituted ketones
- substituted naphthoquinones
- substituted aliphatic nitriles
- substituted aromatic nitriles
- substituted oxadiazoles
- substituted oxadiaziones
- substituted oxadiazolidine diones
- substituted oxadiazine diones
- substituted phenols and their salts and esters
- substituted phosphonic acids and their salts, esters and amides
- substituted phosphonium chlorides
- substituted phosphonalkyl glycines
- substituted phosphites
- substituted phosphoric acids and their salts, esters and amides
- substituted piperidines
- substituted pyrazoles
- substituted pyrazole alkylcarboxylic acids and their salts, esters and amides
- substituted pyrazolium salts
- substituted pyrazolium alkyl sulfates
- substituted pyridazines
- substituted pyridazones
- substituted pyridine carboxylic acids and their salts, esters and amides
- substituted pyridines
- substituted pyridine carboxylates
- substituted pyridinones
- substituted pyrimidines
- substituted pyrimidones
- substituted pyrrolidine carboxylic acid and its salts, esters and amides
- substituted pyrrolidines
- substituted pyrrolidones
- substituted arylsulfonic acids and their salts, esters and amides
- substituted styrenes
- substituted tetrahydrooxadiazine diones
- substituted tetrahydroxadiazole diones
- substituted tetrahydromethanoindenes
- substituted tetrahydroxadiazole thiones
- substituted tetrahydrothiadiazine thiones
- substituted tetrahydrothiadiazole diones
- substituted aromatic thiocarbonylamides
- substituted thiocarboxylic acids and their salts, esters and amides
- substituted thiol carbamates
- substituted thioureas
- substituted thiophosphoric acids and their salts, esters and amides
- substituted triazines
- substituted triazoles
- substituted uracils, and
- substituted uretidine diones.

The last-mentioned herbicidal compounds may also be applied before or after the active ingredients or compositions thereof according to the invention.

These agents may be added to the herbicides according to the invention in a ratio by weight of from 1:10 to 10:1. The same applies to oils, fungicides, nematocides, insecticides, bactericides, antidotes and growth regulators.

The new compositions have a strong herbicidal action and may therefore be used as weedkillers or for controlling the growth of unwanted plants. Whether the new active ingredients are used as total or selective agents depends in essence on the amount of ingredient used per unit area.

By weeds and unwanted plant growth are meant all monocotyledonous and dicotyledonous plants which grow in loci where they are not desired.

The agents according to the invention may therefore be used for controlling for instance

| Gramineae, such as | |
|---|---|
| Cynodon spp. | Dactylis spp. |
| Digitaria spp. | Avena spp. |
| Echinochloa spp. | Bromus spp. |
| Setaria spp. | Uniola spp. |
| Panicum spp. | Poa spp. |
| Alopecurus spp. | Leptochloa spp. |
| Lolium spp. | Brachiaria spp. |

-continued

Sorghum spp.
Agropyron spp.
Phalaris spp.
Apera spp.
etc.;
Cyperaceae, such as
   Carex spp.
   Cyperus spp.
   etc.;
dicotyledonous weeds, such as
Malvaceae, e.g.,
   Abutilon theoprasti
   Sida spp.
   etc.;
Compositae, such as
   Ambrosia spp.
   Lactuca spp.
   Senecio spp.
   Sonchus spp.
   Xanthium spp.
   Iva spp.
   Galinsoga spp.
   Taraxacum spp.
   Chrysanthemum spp.
   Cirsium spp.
Convolvulaceae, such as
   Convolvulus spp.
   Ipomoea spp.
   etc.;
Cruciferae, such as
   Barbarea vulgaris
   Brassica spp.
   Capsella spp.
   Sisymbrium spp.
   Thlaspi spp.
   Sinapis arvensis
   etc.;
Geraniaceae, such as
   Erodium spp.
   etc.;
Portulacaceae, such as
   Portulaca spp.
Primulaceae, such as
   Anagallis arvensis
   etc.;
Rubiaceae, such as
   Richardia spp.
   Galium spp.
Scrophulariaceae, such as
   Linaria spp.
   Veronica spp.
Solanaceae, such as
   Physalis spp.
   Solanum spp.
   etc.;
Urticaceae, such as
   Urtica spp.
Violaceae, such as
   Viola spp.
Zygophyllaceae, such as
   Tribulus terrestris
Euphorbiaceae, such as
   Mercurialis annua
Umbelliferae, such as
   Daucus carota
   Aethusa cynapium
Commelinaceae, such as
   Commelina spp.
Labiatae, such as
   Lamium spp.
   etc.;
Leguminosae, such as
   Medicago spp.
   Trifolium spp.
   Vicia spp.
   etc.;
Plantaginaceae, such as
   Plantago spp.
Polygonaceae, such as
   Polygonum spp.
   Rumex spp.
Aizoaceae, such as
   Mollugo verticillata
Amaranthaceae, such as
   Amaranthus spp.
Boraginaceae, such as
   Amsinckia spp.

Eleusine spp.
Cenchrus spp.
Eragrostis spp.
Phragmites communis

Eleocharis spp.
Scirpus spp.

Hibiscus spp.
Malva spp.

Centaurea spp.
Tussilago spp.
Lapsana communis
Tagetes spp.
Erigeron spp.
Anthemis spp.
Matricaria spp.
Artemisia spp.
Bidens spp.
etc.;

Cuscuta spp.
Jaquemontia tamnifolia

Arabidopsis thaliana
Descurainia spp.
Draba spp.
Coronopus didymus
Lepidium spp.
Raphanus spp.

Geranium spp.

etc.;

Lysimachia spp.

Diodia spp.
etc.;

Digitalis spp.
etc.;

Nicandra spp.
Datura spp.

etc.;

etc.;

etc.;

Euphorbia spp.

Ammi majus
etc.;

etc.;

Galeopsis spp.

Sesbania exaltata
Cassia spp.
Lathyrus spp.

etc.;

Fagopyrum spp.
etc.;

etc.;

etc.;

Anchusa spp.

-continued

Myostis spp.
   etc.;
Caryophyllaceae, such as
   Stellaria spp.
   Spergula spp.
   Saponaria spp.
   Scleranthus annuus
Chenopodiaceae, such as
   Chenopodium spp.
   Kochia spp.
   Salsola Kali
Lythraceae, such as
   Cuphea spp.
Oxalidaceae, such as
   Oxalis spp.
Ranunculaceae, such as
   Ranunculus spp.
   Delphinium spp.
Papaveraceae, such as
   Papaver spp.
   etc.;
Onagraceae, such as
   Jussiaea spp.
Rosaceae, such as
   Alchemillia spp.
   etc.;
Potamogetonaceae, such as
   Potamogeton spp.
Najadaceae, such as
   Najas spp.
Equisetaceae
   Equisetum spp.
Marsileaceae, such as
   Marsilea quadrifolia
Polypodiaceae,
   Pteridium quilinum
Alismataceae, such as
   Alisma spp.
   etc.

Lithospermum spp.

Silene spp.
Cerastium spp.
Agrostemma githago
etc.;

Atriplex spp.
Monolepsis nuttalliana
etc.;

etc.;

Adonis spp.
etc.;

Fumaria offinicalis etc.;

Potentilla spp.

etc.;

etc.;

etc.;

etc.;

Sagittaria sagittifolia

The herbicides according to the invention may be employed in cereal crops such as Avena spp.
   Triticum spp.
   Hordeum spp.
   Secale spp.
   Saccharum offinicarum
and in dicotyledon crops such as
Cruciferae, e.g.
   Brassica spp.
   Sinapis spp.
Compositae, e.g.
   Lactuca spp.
   Helianthus spp.
Malvaceae, e.g.
   Gossypium hirsutum
Leguminosae, e.g.
   Medicago spp.
   Trifolium spp.
   Pisum spp.
Chenopodiaceae, e.g.
   Beta vulgaris
   Spinacia spp.
Solanaceae, e.g.
   Solanum spp.
   Nicotiania spp.
Linaceae, e.g.
   Linum spp.
Umbelliferae, e.g.
   Petroselinum spp.
   Daucus carota
Rosaceae, e.g.
Cucurbitaceae, e.g.
   Cucumis spp.
Liliaceae, e.g.
   Allium spp.
Vitaceae, e.g.
   Vitis vinifera
Bromeliaceae, e.g.
   Ananas sativus.

Sorghum
Zea mays
Panicum miliaceum
Oryza spp.

Raphanus spp.
Lepidium spp.

Carthamus spp.
Scorzonera spp.

Phaseolus spp.
Arachis spp.
Glycine max.

Capsicum annuum

Apium graveolens

Fragaria

Cucurbita spp.

The amount used of the agents according to the invention may vary and depends in essence on the type of effect to be achieved; it is generally from 0.1 to 15 (and more), preferably from 0.2 to 6, kg per hectare of active ingredient. The agents according to the invention may be used once or several times before or after planting, before sowing, and before, during or after emergence of the crop plants and unwanted plants.

EXAMPLE 11

In the greenhouse, the plants cotton (Gossypium hirsutum) and wild mustard (Sinapis arvensis) were treated at a growth height of from 2 to 10 cm with 1 kg/ha of each of the following active ingredients, each being dispersed or emulsified in 500 liters of water per hectare:

I  1-chloromethyl-3-isopropyl-2,1,3-benzothiadiazin-(4)-one-2,2-dioxide

IX  3isopropyl-2,1,3-benzothiadiazine-(4)-one-2,2-dioxide.

After 2 to 3 weeks it was ascertained that active ingredient I was better tolerated by the crop plant and had the same herbicidal action as compound IX.

| Active ingredient kg/ha | I 1 | IX 1 |
|---|---|---|
| Crop plant: | | |
| Gossypium hirsutum | 0 | 30 |
| Unwanted plant: | | |
| Sinapis arvensis | 98 | 100 |

0 = no damage
100 = complete destruction

EXAMPLE 12

In the greenhouse, the plants rice (Oryza satina), Indian corn (Zea mays), soybeans (Glycine max.), wheat (Triticum aestivum), barley (Hordeum vulgare), rye (Secale cereale), wild mustard (Sinapis arvensis) and yellow nutsedge (Cyperus esculentus) were treated at a growth height of from 3 to 23 cm with 4 kg/ha of each of the following compounds, each being dispersed or emulsified in 500 liters of water per hectare:

I  1-chloromethyl-3-isopropyl-2,1,3-benzothiadiazin-(4)-one-2,2-dioxide

II  1-0,0-dimethylphosphorodithio)-methyl-3-isopropyl-2,1,3-benzothiadizin-(4)-one-2,2-dioxide III  1-(2',4',6'-trichlorophenoxy)-methyl-3-isopropyl-2,1,3-benzothiadiazin-(4)-one-2,2-dioxide.

After 2 to 3 weeks it was ascertained that the active ingredients had excellent crop compatability and a good herbicidal action.

The results are given below:

| Active ingredient kg/ha | I 4 | II 4 | III 4 |
|---|---|---|---|
| Crop plants: | | | |
| Oryza sativa | 0 | 0 | 0 |
| Zea mays | 0 | 0 | 0 |
| Glycine max. | 0 | 0 | 0 |
| Triticum aestivum | 0 | 0 | 0 |
| Hordeum vulgare | 0 | 0 | 0 |
| Secale cereale | 0 | 0 | 0 |
| Unwanted plants: | | | |
| Sinapis arvensis | 100 | 100 | 100 |
| Cyperus esculentus | 80 | — | 70 |

0 = no damage
100 = complete destruction

EXAMPLE 13

In the greenhouse, soil in pots was sown with seeds of rice (Oryza sativa) and wild mustard (Sinapis arvensis).

The soil was then immediately treated with 5 kg/ha of II 1-(O,O-dimethylphosphorodithio)-methyl-3-isopropyl-2,1,3-benzothiadiazin-(4)-one-2,2-dioxide dispersed or emulsified in 500 liters of water per hectare.

After 4 to 5 weeks it was ascertained that the active ingredient had excellent crop plant compatibility and a strong herbicidal action.

| Active ingredient kg/ha | II 5 |
|---|---|
| Crop plant: | |
| Oryza sativa | 0 |
| Unwanted plant: | |
| Sinapis arvensis | 100 |

0 = no damage
100 = complete destruction

The biological action of the following compounds corresponds to that of the active ingredients of the invention illustrated in Examples 11, 12 and 13:

1-(p-nitrophenoxy)-methyl-3-isopropyl-2,1,3-benzothiadiazin-(4)-one-2,2-dioxide 1-(phenoxy)-methyl-3-isopropyl-2,1,3-benzothiadiazin-(4)-one-2,2-dioxide 1-(3',3'-dimethylureido-1'-m-phenoxy)-methyl-3-isopropyl-2,1,3-benzothiadiazin-(4)-one-2,2-dioxide 1-(3'-methoxycarbonylaminphenoxy)-methyl-3-isopropyl-2,1,3-benzothiadiazin-(4)-one-2,2-dioxide 1-(O,O-diethylphosphorodithio)-methyl-3-isopropyl-2,1,3-benzothiadiazin-(4)-one-2,2-dioxide.

EXAMPLE 14

90 parts of weight of compound I is mixed with 10 parts by weight of N-methyl-α-pyrrolidone. A mixture is obtained which is suitable for application in the form of very fine drops.

EXAMPLE 15

20 parts by weight of compound I is dissolved in a mixture consisting of 80 parts by weight of xylene, 10 parts by weight of the adduct of 8 to 10 moles of ethylene oxide to 1 mole of oleic acid-monoethanolamide, 5 parts by weight of the calcium salt of dodecylbenzenesulfonic acid, and 5 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 16

20 parts by weight of compound II is dissolved in a mixture consisting of 40 parts by weight of cyclohexanone, 30 parts by weight of isobutanol, 20 parts by weight of the adduct of 7 moles of ethylene oxide to 1 mole of isooctylphenol, and 10 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 17

20 parts by weight of compound I is dissolved in a mixture consisting of 25 parts by weight of cyclohexanol, 65 parts by weight of a mineral oil fraction having a boiling point between 210° and 280° C, and 10 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 18

20 parts by weight of compound II is well mixed with 3 parts by weight of the sodium salt of diisobutylnaphthalene-α-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquid is obtained containing 0.1% by weight of the active ingredient.

EXAMPLE 19

3 parts by weight of compound I is intimately mixed with 97 parts by weight of particulate kaolin. A dust is obtained containing 3% by weight of the active ingredient.

EXAMPLE 20

30 parts by weight of compound II is intimately mixed with a mixture consisting of 92 parts by weight of powdered silica gel and 8 parts by weight of paraffin oil which has been sprayed onto the surface of this silica gel. A formulation of the active ingredient is obtained having good adherence.

EXAMPLE 21

In the greenhouse various plants were treated at a growth height of from 3 to 15 cm with the following active ingredients, each being emulsified or dispersed in 500 liters of water per hectare:

IV  1-(formyloxy)-methyl-3-isopropyl-2,1,3-benzothiadiazin-(4)-one-2,2-dioxide

V   1-(cyclohexanoyloxy)-methyl-3-isopropyl-2,1,3-benzothiadiazin-(4)-one-2,2-dioxide VI  1-(benzoyloxy)-methyl-3-isopropyl-2,1,3-benzothiadiazin-(4)-one-2,2-dioxide VII 1-(p-methoxybenzoyloxy)-methyl-3-isopropyl-2,1,3-benzothiadiazin-(4)-one-2,2-dioxide VIII 1-(methoxyacetoxy)-methyl-3-isopropyl-2,1,3-benzothiadiazin-(4)-one-2,2-dioxide X   1-(isobutyryloxy)-mthyl-3-isopropyl-2,1,3-benzothiadiazin-(4)-one-2,2-dioxide    -(isobutyryloxy)-methyl- X   1-chloromethyl-3-isopropyl-2,1,3-benzothiadiazin-(4)-one-2,2-dioxide After 2 to 3 weeks it was ascertained that the active ingredients had a strong herbicidal action and good crop plant compatibility.

The results are given below:

| Active ingredient kg/ha | IV 3 | V 3 | VI 3 | VII 3 | VIII 3 | X 3 | XI 3 |
|---|---|---|---|---|---|---|---|
| Crop plant: | | | | | | | |
| *Triticum aestivum* | 0 | 0 | 0 | 0 | 0 | 0 | 0 |
| Unwanted plant: | | | | | | | |
| *Sinapis alba* | 100 | 95 | 100 | 100 | 100 | 100 | 100 |

0 = no damage
100 = complete destruction

The following compounds have a corresponding action:

1-(chloroacetoxy)-methyl-3-isopropyl-2,1,3-benzothiadiazin-(4)-one-2,2-dioxide 1-(acryloyloxy)-methyl-3-isopropyl-2,1,3-benzothiadiazin-(4)-2,2-dioxide 1-(phenylthio)-methyl-3-isopropyl-2,1,3-benzothiadiazin-(4)-one-2,2-dioxide 1-(acetoxy)-methyl-3-isopropyl-2,1,3-benzothiadiazin-(4)-one-2,2-dioxide    1-(O,O-dimethylphosphorothio)-S-methyl-3-isopropyl-2,1,3-benzothiadiazin-(4)-one-2,2-dioxide.

EXAMPLE 22

In the greenhouse, various test plants, separated by species, were cultivated in pots. They were treated at a growth height of from 5 to 15 cm with the following active ingredients, each being dispersed or emulsified in 500 liters of water per hectare:

I  1-(cyclohexanoyloxy)-methyl-3-isopropyl-2,1,3-benzothiadiazin-(4)-one-2,2-dioxide II 1-(formyloxy)-methyl-3-isopropyl-2,1,3-benzothiadiazin-(4)-one-2,2-dioxide.

The plants and application rates employed and the results obtained will be apparent from the following table. Assessment took place 2 to 4 weeks after treatment.

The results demonstrate the utility of the substances for combatting broadleaved weeds in important cereals.

| Active ingredient | I | | | | | II | | | | |
|---|---|---|---|---|---|---|---|---|---|---|
| kg/ha | 0.25 | 0.5 | 1.0 | 2.0 | 4.0 | 0.25 | 0.5 | 1.0 | 2.0 | 4.0 |
| *Avena sativa* | — | 0 | 0 | 0 | — | — | 0 | 0 | 0 | — |
| *Triticum aestivum* | — | 0 | 0 | 0 | — | — | 0 | 0 | 0 | — |
| *Zea mays* | — | 10 | 10 | 10 | 10 | — | 10 | 10 | 20 | 20 |
| *Abutilon theophrastii* | 70 | 95 | 95 | 95 | — | 20 | 40 | 80 | 90 | — |
| *Ammannia coccinea* | 62 | 62 | 92 | 92 | — | 68 | 68 | 92 | 92 | — |
| *Chrysanthemum segetum* | 52 | 68 | 95 | 95 | — | 52 | 58 | 70 | 95 | — |
| *Matricaria chamomiua* | 95 | 95 | 95 | 95 | — | 25 | 90 | 90 | 95 | — |
| *Sida spinosa* | 20 | 40 | 50 | 70 | — | 10 | 10 | 20 | 30 | — |
| *Sinapis alba* | 65 | 70 | 70 | 95 | — | 95 | 100 | 100 | 100 | — |

0 = no damage
100 = complete destruction

EXAMPLE 23

In the greenhouse, rice, soybeans and hemp sesbania were cultivated in separate pots. They were treated at a growth height of from 6 to 10 cm with the following active ingredients, each being emulsified or dispersed in 500 liters of water per hectare:

I   1-(cyclohexanyloxy)-methyl-3-isopropyl-2,1,3-benzothiadiazin-(4)-one-2,2-dioxide II  1-(formyloxy)-methyl-3-isopropyl-2,1,3-benzothiadiazin-(4)-one-2,2-dioxide III 3-isopropyl-2,1,3-benzothiadiazin-(4)-one-2,2-dioxide (prior art)

During the experiment the pots were kept in a warm and moist place. Assessment was carried out 3 weeks after treatment.

The results are given below. It will be seen that the new active ingredients are suitable for controlling Sesbania exaltata, a broadleaved weed belonging to the Leguminosae family, in soybeans, which are also leguminous. The compounds may further be used for controlling unwanted broadleaved species in rice.

| Active ingredient | I | | | | II | | | | III (prior art) | | | |
| --- | --- | --- | --- | --- | --- | --- | --- | --- | --- | --- | --- | --- |
| kg/ha | 0.25 | 0.5 | 1.0 | 2.0 | 0.25 | 0.5 | 1.0 | 2.0 | 0.25 | 0.5 | 1.0 | 2.0 |
| Glycine max. | — | 10 | 5 | 10 | — | 10 | 5 | 15 | — | 0 | 0 | 10 |
| Oryza sativa | — | 0 | 0 | 10 | — | 0 | 0 | 10 | — | 0 | 0 | 10 |
| Sesbania exaltata | 20 | 85 | 85 | 85 | 48 | 85 | 85 | 88 | 0 | 0 | 0 | 10 |

0 = no damage
100 = complete destruction

We claim:

1. A substituted 2,1,3-benzothiadiazin-(4)-one-2,2-dioxide of the formula

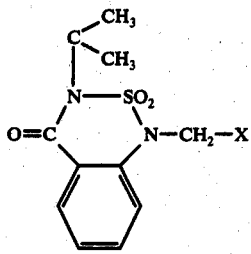

where X denotes halogen or a

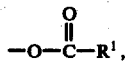

—O—$R^2$, —$SR^3$, or 2,4-dinitro-6-bromoanilino, o-cyanoanilino, o-nitroanilino, o-bromo-p-nitroanilino, and N-methyl-(o-bromo-p-nitroanilino), $R^1$ denoting alkyl, alkenyl, alkynyl, alkoxyalkyl, haloalkyl, cycloalkyl, aralkyl, or aryl, $R^2$ denoting O,O-dialkylthiophosphoro, O,S-dialkylphosphoro, S,S-dialkylphosphoro, O,O-dialkylthiophosphoro, O,S-dialkylthiophosphoro, S,S-dialkylthiophosphoro, aralkyl, aryl, or phenyl substituted by chlorine, nitro, lower alkyl, lower alkoxy, lower alkoxycarbonylamino or diloweralkylureido and $R^3$ having the same meanings as $R^1$ and additionally denoting O,O-dialkylthiophosphoro, O,S-dialkylthiophosphoro, S,S-dialkylthiophosphoro, O,O-dialkylphosphoro, O,S-dialkylphosphoro and S,S-dialkylphosphoro.

2. 1-(chloromethyl)-3-isopropyl-2,1,3-benzothiadiazin-(4)-one-2,2-dioxide.

3. 1-(formyloxy)-methyl-3-isopropyl-2,1,3-benzothiadiazin-(4)-one-2,2-dioxide.

4. 1-(isobutyryloxy)-methyl-3-isopropyl-2,1,3-benzothiadiazin-(4)-one-2,2-dioxide.

5. 1-(cyclohexanoyloxy)-methyl-3-isopropyl-2,1,3-benzothiadiazin-(4)-one-2,2-dioxide.

6. 1-(benzoyloxy)-methyl-3-isopropyl-2,1,3-benzothiadiazin-(4)-one-2,2-dioxide.

7. 1-(p-methoxybenzoyloxy)-methyl-3-isopropyl-2,1,3-benzothiadiazin-(4)-one-2,2-dioxide.

8. 1-(2',4',6'-trichlorophenoxy)-methyl-3-isopropyl-2,1,3-benzothiadiazin-(4)-one-2,2-dioxide.

9. 1-(O,O-dimethylphosphorodithio)-methyl-3-isopropyl-2,1,3-benzothiadiazin-(4)-one-2,2-dioxide.